United States Patent [19]

Atadan

[11] Patent Number: 4,937,336

[45] Date of Patent: Jun. 26, 1990

[54] PROCESS FOR THE PREPARATION OF HEXAMETHYLENE IMINE

[75] Inventor: Erdem M. Atadan, Wilmington, Del.

[73] Assignee: E. I. du Pont de Nemours and Company, Wilmington, Del.

[21] Appl. No.: 279,920

[22] Filed: Dec. 5, 1988

[51] Int. Cl.$^5$ .............................................. C07D 295/02
[52] U.S. Cl. .................................... 540/612; 540/450; 546/184
[58] Field of Search .................... 540/612; 840/450; 546/184

[56] References Cited

U.S. PATENT DOCUMENTS 4,001,213  1/1977  Hershman et al. ................... 540/612

FOREIGN PATENT DOCUMENTS 196866  11/1984  Japan ................................. 540/612

Primary Examiner—William R. Dixon, Jr.
Assistant Examiner—Jerry D. Johnson

[57] ABSTRACT

A process for the preparation of hexamethylene imine from hexamethylene diamine by the vapor phase reaction in the presence of water, hydrogen, and a palladium catalyst.

6 Claims, No Drawings

PROCESS FOR THE PREPARATION OF HEXAMETHYLENE IMINE

FIELD OF THE INVENTION

This invention relates to the preparation of hexamethyleneimine, also known as perhydroazepine, from hexamethylene diamine at high conversion and at high yield.

BACKGROUND OF THE INVENTION

The preparation of hexamethyleneimine by the catalytic reaction of hexamethylene diamine and hydrogen in the vapor phase is described in U.S. Pat. No. 4,001,213. The preferred catalysts disclosed are nickel, copper, cobalt and iron, but novel metals of Group 8 are also disclosed; i.e. rhodium, palladium and platinum catalyst. Example 6 of this patent shows a catalyst of palladium and cobalt. The example concludes with the statement: "While palladium increased the activity of the catalyst system it drastically reduces the selectivity to the desired imine product".

SUMMARY OF THE INVENTION

The present invention is a process for the preparation of hexamethyleneimine by contacting a gaseous mixture containing 1,6-hexamethylene diamine, water and hydrogen with a solid palladium catalyst at a temperature of 160° to 260° C. at a pressure of 0 to 100 psig.

If desired, the gaseous mixture may also contain methane, ammonia, nitrogen, or other inert gases. The methane or ammonia, apparently pass through the reactor without directly participating in reaction, but increase the activity of the catalyst, especially at higher pressures of operations.

The palladium catalyst comprises an inert substrate, on which is dispersed palladium metal. Normally the amount of palladium in the catalyst is about 0.1 to 10% by weight palladium.

The amount of water in the gaseous mixture may vary widely. Normally the gaseous mixture will be made by vaporizing an aqueous mixture of water and hexamethylene diamine. The amount of water in this aqueous mixture may vary from 1 to 40% by weight.

The amount of hydrogen in the gaseous mixture may also vary widely but is usually present in an amount, on a molar basis, about 5 to 15 times the amount of hexamethylene diamine. The amount of hydrogen employed may be lowered if methane, ammonia, nitrogen or other inert gas is also present in the gaseous mixture. Ammonia is a product of reaction; but, added $NH_3$ or methane or nitrogen may be used in high pressure operations to reduce the partial pressure of $H_2$.

DETAILED DESCRIPTION

The process of the invention may be carried out by passing a gaseous mixture of 1,6-hexamethylene diamine, water and hydrogen through a reactor filled with loosely packed palladium metal catalyst. A suitable laboratory reactor is a metal tube having an internal diameter of 0.5 to 1 inch. The tube may be mounted vertically, or horizontally. If it is mounted vertically it is preferred to pass the gaseous mixture downwardly through the reactor.

The palladium metal catalyst comprises an inert substrate having dispersed palladium metal on its surface. The inert substrate can be aluminum oxide, glass, silica, etc. Aluminum oxide in the form of spheres having a diameter of about 1/20 to ¼ inch is a preferred substrate.

The palladium metal content of the catalyst should be in the range of 0.1 to 10% by weight of the catalyst, preferably 0.5 to 2% by weight. The palladium need not completely coat the substrate; finely dispersed particles of palladium metal on the substrate are satisfactory.

After the gaseous mixture passes through the reactor, the mixture is cooled to condense a hexamethylene imine containing liquid, the hydrogen removed and recycled to the feed, and the liquid separated into its components by conventional techniques.

EXAMPLE

A five foot long thin walled stainless steel tube having an external diameter of 0.5 inch and an internal diameter of 0.42 inch was loaded with 110 grams of palladium metal on $Al_2O_3$ spheres having a diameter of 1/16 inch. The palladium content was 0.5% by weight. The palladium was in the form of a thin coating on the surface of the $Al_2O_3$ spheres. The reactor was heated to 220° C. by oil in an external jacket, and a vapor of 70% 1,6-hexamethylene diamine and 30% water was fed to the top of the reactor along with hydrogen, and in some runs ammonia, and in some runs methane. The reaction is isothermal. The conditions and results are shown in the table below.

| RUN | PRES. PSIG | FLOWRATES 70% HMD ML/HR | $H_2$ CC/MIN | $NH_3$ CC/MIN | % HMD CONV. | % HMI YIELD |
|---|---|---|---|---|---|---|
| 1 | 20 | 61 | 2000 | 0 | 99.8 | 92.6 |
| 2 | 20 | 61 | 2000 | 0 | 99.8 | 92.3 |
| 3 | 20 | 50 | 2000 | 0 | 99.9 | 91.9 |
| 4 | 60 | 50 | 2000 | 0 | 83.0 | 96.0 |
| 5 | 80 | 50 | 2000 | 0 | 69.9 | 95.2 |
| 6 | 60 | 50 | 1700 | 295 | 97.6 | 93.9 |
| 7 | 60 | 50 | 1500 | 490 | 99.1 | 94.6 |
| 8 | 60 | 50 | 1250 | 735 | 99.7 | 88.5 |
| 9 | 60 | 50 | 500 | 1470 | 99.7 | 76.7 |
| 10 | 80 | 50 | 1700 | 295 | 78.2 | 94.7 |
| 11 | 80 | 50 | 1500 | 490 | 87.4 | 94.3 |
| 12 | 80 | 50 | 1250 | 735 | 97.3 | 94.5 |
| 13 | 60 | 75 | 500 | 1470 | 99.6 | 83.3 |
| 14 | 80 | 50 | 2000 | 0000 | 63.5 | 83.3 |
| 15 | 80 | 50 | 2000 | 0000 | 51.6 | 90.6 |
| 16 | 80 | 50 | 1700 | 300 | 56.4 | 92.6 |
| 17 | 80 | 50 | 1500 | 500 | 67 | 91 |
| 18 | 80 | 50 | 1250 | 750 | 85.3 | 91.6 |
| 19 | 80 | 50 | 1000 | 1000 | 95.8 | 91.8 |
| 20 | 80 | 50 | 1000 | 1000 | 97.8 | 91.6 |

I claim:

1. A process for the preparation of hexamethyleneimine which comprises contacting hydrogen and a gaseous mixture, wherein said gaseous mixture is made by vaporizing a mixture of 99-60% hexamethylene diamine and 1-40% water, with a solid palladium metal catalyst containing 0.1 to 10% palladium on an inert substrate at a temperature of 160 to 260 degrees C. and a pressure of 1 to 100 psig.

2. The process of claim 1 in which the gaseous mixture also contains at least one member selected from the class consisting of ammonia, methane, and nitrogen.

3. The process of claim 2 in which the palladium catalyst comprises an inert substrate selected from the class consisting of aluminum oxide, glass and silica and 0.1 to 10% by weight palladium metal.

4. The process of claim 1 in which the ratio, on a molar basis, of hydrogen to hexamethylene diamine is in the range of about 5 to 15.

5. The process of claim 3 in which the inert substrate is $Al_2O_3$.

6. The process of claim 1 in which the gaseous mixture is passed through a tube reactor containing the catalyst.

* * * * *